United States Patent [19]
Leibinger

[11] Patent Number: 4,512,498
[45] Date of Patent: Apr. 23, 1985

[54] STERILIZABLE CONTAINER

[75] Inventor: Karl Leibinger, Mühlheim, Fed. Rep. of Germany

[73] Assignee: Karl Liebinger Medizintechnik GmbH & Co., Muhlheim, Fed. Rep. of Germany

[21] Appl. No.: 614,109

[22] Filed: May 24, 1984

[30] Foreign Application Priority Data

Oct. 21, 1983 [DE] Fed. Rep. of Germany ....... 3338371

[51] Int. Cl.³ .............................................. B65D 51/16
[52] U.S. Cl. .................................... 220/371; 220/366; 220/367
[58] Field of Search ......................... 220/366, 367, 371

[56] References Cited

U.S. PATENT DOCUMENTS 2,732,092 1/1956 Lawrence ........................... 220/371
3,083,861 4/1963 Amberg et al. ..................... 220/371

Primary Examiner—George T. Hall
Attorney, Agent, or Firm—Merchant, Gould, Smith, Edell, Welter & Schmidt

[57] ABSTRACT

Figure 1:
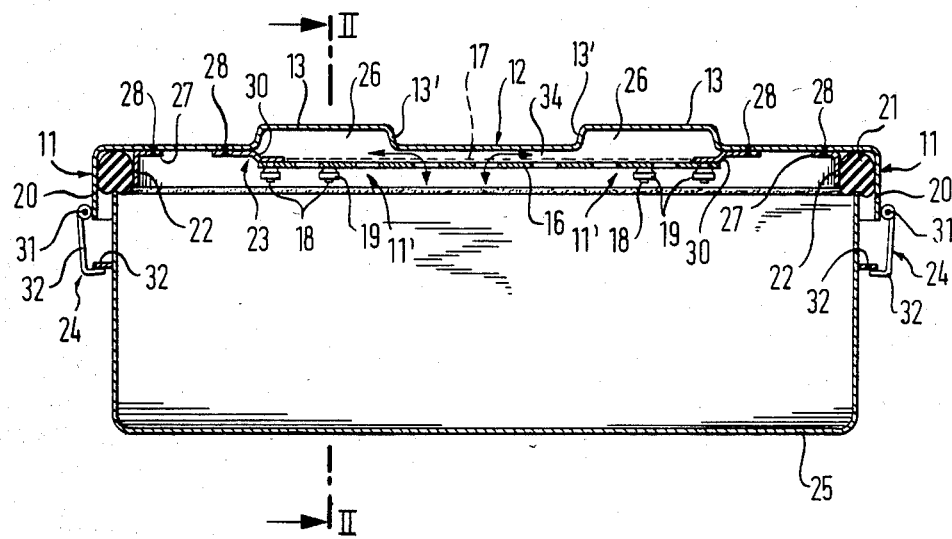

A sterilizable container consists of a container part (25) and a cover (12) mounted thereon via a ring seal (11). Bulges (13) provided in the cover (12) and a filter or valve arrangement (16, 17, 18, 19) mounted internally thereon make a germ-free gas exchange between the interior of the container and the atmosphere possible (FIG. 1).

18 Claims, 6 Drawing Figures

STERILIZABLE CONTAINER

The invention relates to a sterilising container comprising a container part which is open at the top and a cover which has no openings and which is sealingly mounted on the container via a ring seal, the cover having a peripheral downwardly extending edge and at least one bulge which extends up to the edge and which forms a free-flow passage from the atmosphere up to a filter or a valve arrangement provided at the inner side of the cover and arranged between the internal chamber of the container and the flow channel.

In a known sterilisable container of this kind the cover consists of an outer closure cover which does not have any openings and an inner intermediate cover which is releasably secured to the outer cover and connected to the container part via the ring seal. The intermediate cover has openings for the passage of vapour in the region of the bulges. The openings are covered over by a filter cloth. In this manner a vapour and air exchange with the environment can take place from the inner chamber of the sterilising container through the openings and the filter cloth and also through the flow passage formed behind the bulges.

A disadvantage of the known sterilising container is the requirement for a special intermediate cover which not only makes manufacture more difficult and expensive but also impairs the handling of the sterilisable container, in particular the cleaning thereof. Moreover, the full cover is relatively heavy due to the combination of an outer cover and an intermediate cover.

The principal object underlying the present invention is to provide a sterilising container of the initially named kind which requires substantially less material, and is therefore lighter, and which is light and easy to handle in particular in the event of cleaning or of replacement of the filter material or valves. At the same time the inner chamber should be capable of being sealed in an absolutely sterile manner against the surrounding atmosphere and problemfree air and vapour exchange should also be possible.

In order to satisfy this object the invention provides that the ring seal is arranged at the inner side of the cover in the corner between the cover surface and the side edge, bridges the bulge and is spaced therefrom; and that the filter and valve arrangement extends in a surface region which is bounded by the seal part which bridges the bulge and by the edges of the bulge which extend within the ring seal, whereby the part of the surface region which is not taken up by the filter or valve arrangement is covered in gas-tight manner.

Thus, in accordance with the invention, the intermediate cover which was previously necessary is done away with all together. The ring seal is, on the contrary, directly secured to the cover which does not have any openings but only the bulges. The ring seal however only contacts the regions of the cover at which there are no bulges and in fact bridges the bulges. In other words the ring seal is arranged as in a customary cover without the bulges, but so that a free-flow channel is formed between the ring seal and the material of the cover through which a vapour and/or air exchange between the atmosphere and the interior of the container can take place via the filter and valve arrangement. In order to reliably avoid the entry of germs it is however necessary that the flow channel inside the bulges which passes the ring seal only leads into the interior of the container part via filter material or a valve, whereas all other surface regions between the interior of the sterilisable container and the flow channel in the bulges must be covered over in gas-tight manner.

As a sealing rope of resilient material is generally not sufficiently stable to bridge the bulges itself a preferred embodiment of the invention provides that the ring seal includes a U-shaped rail which is directly secured to the inner side of the cover, other than in the region of the bulge, and that a sealing rope is inserted into the rail and preferably secured there. Thus in this arrangement a U-shaped rail, which can readily be made very stable, form the bridges over the bulges so that a very good sealing action between the sealing rope and the upper edge of the container part is ensured even in the region of the bulges.

A further development of the invention is characterised in that a respective sheet metal bridging plate is secured to each of the parts of the U-shaped rail which bridge the bulge, with each bridging plate extending over the associated bulge and being sealingly connected with the edges thereof; and in that the filter or valve arrangement is sealingly secured to these bridging plates and to the regions of the cover adjacent the bulge. In this manner it is ensured that, inside the ring seal in the region of the bulges, vapour and air must flow through the filter or valve arrangement.

In accordance with an advantageous practical embodiment the filter or valve arrangement is formed by a perforated metal sheet and by a filter cloth which at least bridges the bulge within the ring seal. This embodiment is expediently so arranged that the perforated sheet has an edge free of perforations which lies on the inner side of the cover outside of the bulge or on the bridging plate which bridge the bulge and which is secured thereto while trapping the filter cloth.

With this embodiment it is preferably arranged, in order to releasably secure the filter cloth and the perforated sheet that threaded securing studs onto which nuts are screwed extend inwardly at right angles to the surface of the cover from the cover or from the bridging plates through corresponding bores of the filter cloth or of the edge of the perforated sheet.

The invention can however also be used for sterilising containers in which the ring seal comprises a sealing rope inserted directly into the corner between the surface of the cover and the edge of the cover, and an inner sheet metal support ring which is secured to the cover and which projects at right angles to the cover surface. In order to support the ring seal in the region of the bulges in problemfree manner in an arrangement of this kind the sheet metal support ring is constructed in the region of the bulge as the one side wall of a U-shaped rail, which is secured to the cover and which bridges the bulge, with the other side wall of the rail extending inside the bulge parallel to the edge of the cover and there supporting the sealing rope laterally from the outside.

A particularly advantageous and practical embodiment is characterised in that a frame which carries the filter or valve arrangement is sealingly secured to the U-shaped rail and to the regions of the cover which surround the bulge or bulges. As the frame is preferably secured both to the cover and to the U-shaped rail by welding the U-shaped rail is additionally braced by the frame.

A further embodiment envisages that a frame which carries the filter or valve arrangement is sealingly secured to the U-shaped rail and to the regions of the cover surrounding the bulges.

It is expedient, both from the technical manufacturing view point and also from the view point of a constant flow cross-section for the bulge to extend up to the lower lip of the edge of the cover.

In order to ensure troublefree securing of the cover to the container part on the one hand, and gas exchange which is as far as possible unhindered on the other hand, a further embodiment provides that the or each bulge extends parallel to the side of the cover which carries the cover securing members. Thus no flow channels open at the side which carries the cover securing members.

It is expedient if the or each bulge is formed by material which is displaced outwardly parallel to itself from the plane of the cover and from the plane of the edge of the cover with this material merging into the material lying in the normal plane of the cover at the edge regions of the respective bulge.

Troublefree flow guidance is ensured when the edges of the bulge are parallel to one another. The edges should preferably extend at right angles to the side or sides of the container where the flow channel opens.

It is particularly advantageous for the or each bulge to extend transversely over the cover to opposite edges thereof and for the bridging plates and U-shaped rails to be correspondingly provided in duplicate. In this manner gas exchange can take place towards the two oppositely disposed edges of the cover.

For stability reasons it is expedient, in particular for rectangular covers, for a plurality of bulges (and in particular two bulges) to be arranged spaced apart in the direction of the longitudinal sides of the cover, preferably parallel to the short sides thereof.

When using several bulges it can be arranged that the frame and the U-shaped rails extend over all bulges and the cover regions that lie therebetween; and that the frame is inwardly joggled in such a way that the filter cloth and the perforated sheet are also spaced from the inner surface of the cover in the region between the bulges. One and the same perforated sheet can thus extend over several spaced apart bulges, whereby flow exchange between neighbouring bulges is possible as a result of the spacing of the perforated sheet and the filter cloth from the cover material.

The invention will now be described by way of example only in the following and with reference to the drawings which show:

FIG. 1 a vertical central longitudinal section of a first embodiment of a sterilising container in accordance with the invention, FIG. 2 a section on the line II—II of FIG. 1, FIG. 3 a view of the cover of the sterilising container of FIGS. 1 and 2 from below, FIG. 4 a vertical central longitudinal section of a further embodiment of a sterilising container in accordance with the invention, FIG. 5 a section of the line V—V of FIG. 4, and FIG. 6 a view of the cover of the sterilising container of FIGS. 4 and 5 from below.

Figure 2:
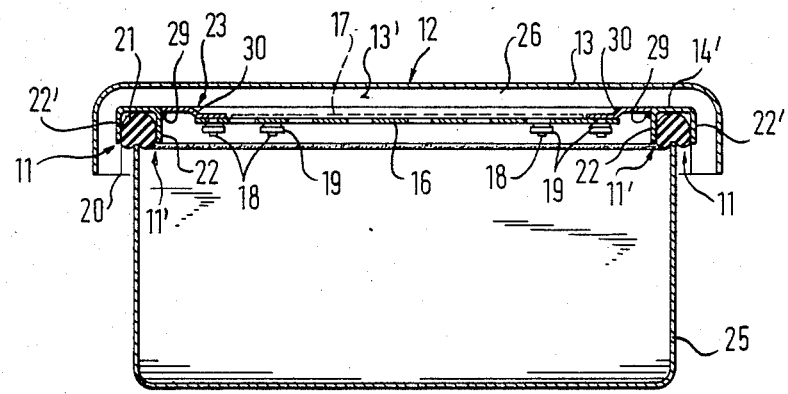
Figure 3:
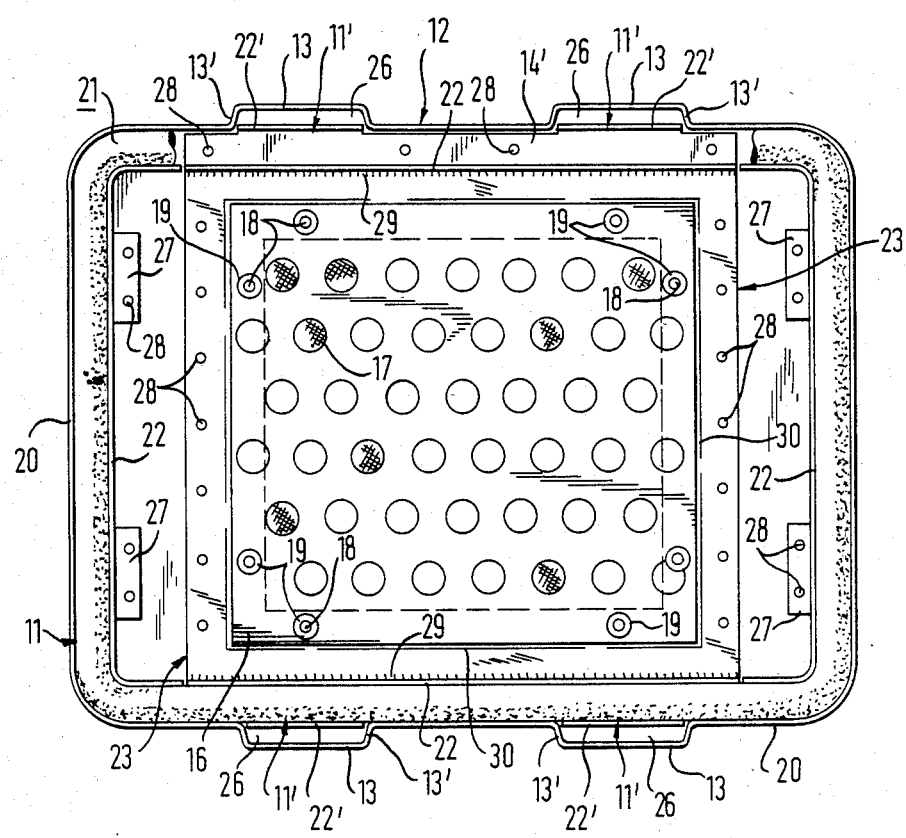

As seen in FIGS. 1 to 3 a container part 25 which has the shape of a parallelepiped and which is open at its top end is covered over at the top by a cover 12. The rectangular cover 12 has two bulges 13 which extend parallel to the short sides of the rectangle and the material of which is outwardly displaced relative to the actual surface of the cover, parallel thereto, by a certain amount. The bulges 13 merge via edge regions 13' into the otherwise flat surface of the cover. Around the cover 12 there is a downwardly turned edge 20 and the bulges 13 continue up to this edge. In this manner flow channels 26 are formed within the cover which run, as a consequence of the extent of the bulges 13 shown in the drawing, from the lower lip of one side edge 20 to the lower lip of the opposite side edge.

A sealing rope 21 is inserted into the inner corner between the cover 12 and the edge 20 and is supported at its inner side by a sheet metal ring support 22 which extends parallel to and spaced from the edge 20. The sealing rope 21 and the sheet metal support ring together form a ring seal 11 which sealingly contacts the upper edge of the container part 25 from above. The sheet metal ring support 22 is secured by angled portions 27 to the interior of the cover by means of spot welds 28.

In the region of the bulges 13 the sheet metal support ring 22 is formed, in accordance with the invention, by a U-shaped rail 14' the central web of which is secured to the cover by spot welds 28. The inner side wall forms the continuation of the sheet metal support ring 22 for the sealing rope 21. The outer side wall 22' of the U-shaped rail 14' is cut away apart from the regions inside the bulges 13. The side walls 22' extend parallel to the edge 20 and continue the latter within the bulges 13, as can be seen in particular from FIG. 3 where the sealing rope 21 is shown broken away at the upper long side of the rectangular cover 12 in order to illustrate the design and arrangement of the U-shaped rail 14'. The construction at the lower long side 3 of the cover 12 in FIG. 3 is the same.

As a result of this construction the ring seal 11 bridges the bulges 13 in the regions 11' in a manner such that the sealing rope 21 is also supported in these regions without problem from three sides so that a good sealing action is obtained in these regions and so that the flow channel 26 is maintained in the regions 11' of the ring seal.

A rectangular frame 23 is provided, in accordance with the invention, at the inner side of the cover in order to allow the flow channel 26 to open into a filter. The long sides of the frame 23 are externally connected via weld seams 29 with the upper webs of the U-shaped rails 14'. The short sides of the frame 23 extend laterally of the bulges 13 over the inner surface of the cover 12 and sealingly contact the same. The rigid connection of the short sides of the frame 23 with the inner surface of the cover is achieved by spot welds 28. In any event a gas tight connection is required here.

As a result of this construction the flow channels 26 merely lead to the internal opening of the frame 23. The frame has a peripherally extending joggled or bent region 30 so that its inner region projects further into the interior of the container. At the inner edge of the joggle the frame 23 carries threaded securing studs 18 which extend at right angles to the surface of the cover and project into the interior of the container. As seen in FIG. 3 these threaded securing studs 18 are uniformly distributed around the periphery of the frame 23. A filter cloth 17 which is dimensioned in accordance with the frame 23 is first placed on the frame 23 from the inside and a correspondingly dimensioned perforated sheet of metal 16 is then arranged thereon. The perforated sheet 16 and the filter cloth 17 have bores corresponding to the threaded securing studs 18 so that they can be accurately fitted onto the frame 23. The filter cloth 17 and the rectangular perforated sheet 16 can be secured to the frame 23 by means of threaded nuts 19.

Cover securing members 24 are provided at the narrow sides of the container as shown in FIG. 1 to sealingly secure the cover 12 to the container part 25. The cover securing member 24 can, for example, comprise a hook part 32 pivotable about the transverse axle 31 on the cover 12 and a corresponding counterelement 33 on the container part 25. The illustration in FIG. 1 is to be understood purely schematically.

The above explained sterilising container of FIGS. 1 to 3 operates as follows: The filter cloth 17 can be exchanged for a new one by releasing the nuts 19 and removing the perforate sheet 16. The perforate sheet 16 is then replaced on the filter cloth 17 mounted on the frame 23 and re-secured by means of the nuts 19. The cover 12 can now be mounted on the container part 25 in the manner illustrated in FIGS. 1 and 2 and secured thereto by means of the clamping elements 24. The sealing rope 21 now lies on all sides, and indeed also in the regions 11' of the ring seal 11 sealingly and with adequate pressure on the container part 25. There is thus a problem-free seal of the gap between the container part 25 and the cover part 12 all around the container. Vapour can however enter into the flow channels 26 through the perforate sheet 16 and the filter cloth 17 and can emerge into the atmosphere through these flow channels 26 around the bridge regions 11' of the ring seal 11 at the lower lip of the edge 20. Flow is also possible in the reverse direction, the air that is however sucked in is however obliged to pass through the filter cloth 17. In this manner the entry of germs into the interior of the container is effectively avoided.

As a result of the joggled region 30 the filter cloth 17 and the perforate sheet 16 are spaced from the inner side of the cover so that a free space 34 is present between the cover 12 and the filter cloth 17, even in the intermediate region of the cover 12 which is not provided with bulges 13. Flow to and from the flow channels 26 in the bulges 13 can also take place in this space 34 in the direction of the arrows. In this manner the region of the filter cloth 17 and of the perforate sheet 16 which lies between the bulges 13 is also utilised, and the flow resistance is correspondingly reduced. The flow in the free space 34 is however only possible in the longitudinal direction of the container to the bulges 13 because the space 34 is sealed at the long sides by the ring seal 11. Only in the region of the bulges 13 does the flow path 26 lead outwardly around the ring seal 11 and past the bridge regions 11'.

Figure 4:
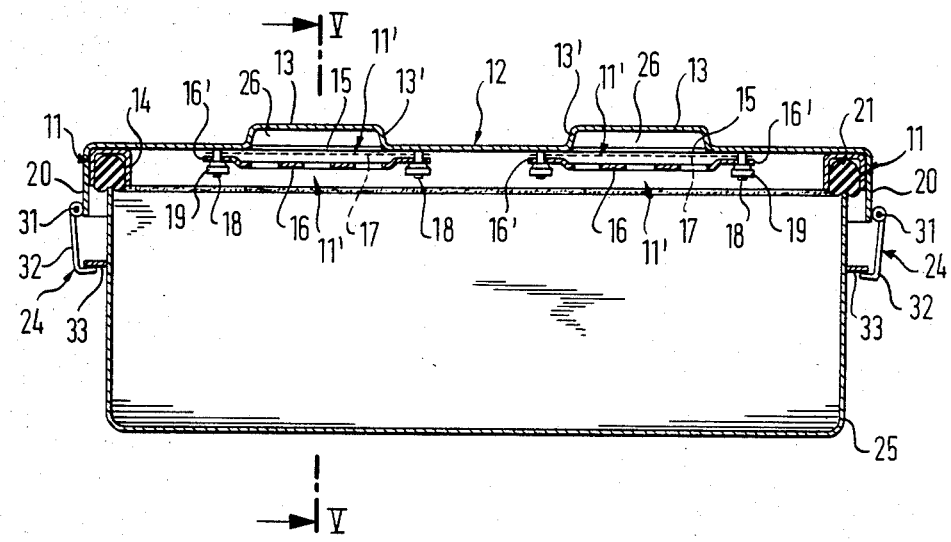
Figure 5:
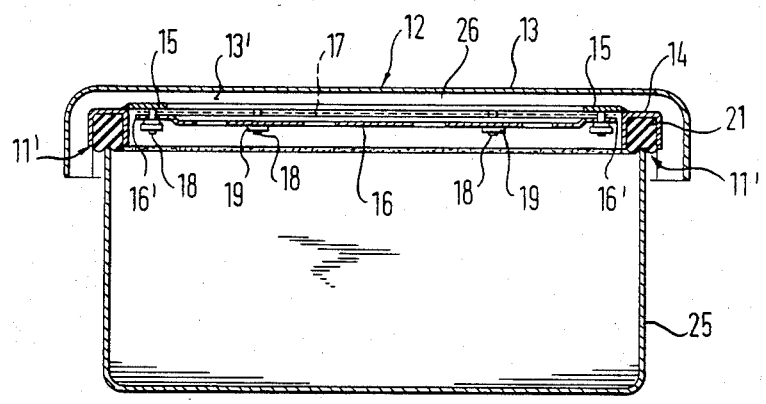
Figure 6:
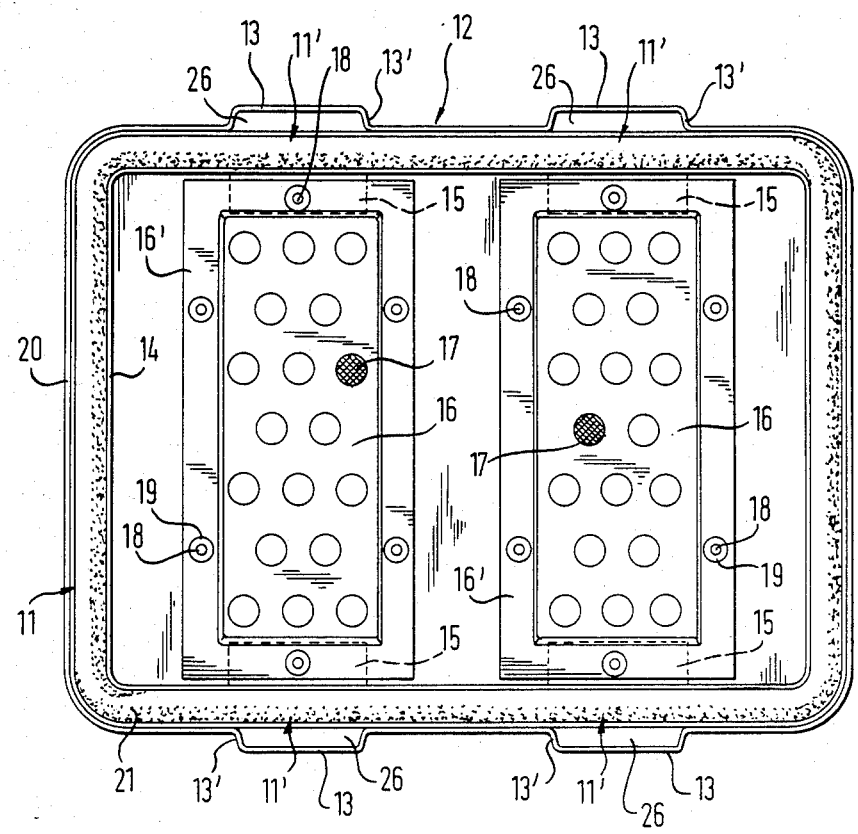

In the further embodiment illustrated in FIGS. 4 to 6 the same reference numerals are used to designate parts which have counterparts in FIGS. 1 to 3.

The embodiment of FIGS. 4 to 6 have the same spaced apart bulges 13 as the previous embodiment. In distinction to the embodiment of FIGS. 1 to 3 the U-shaped rail is however here secured all around the inner side of the cover 12. The U-shaped rail 14 once again bridges the flow channels 26 in the bulges 13 in the regions 11'.

A sheet metal bridging plate 15 is welded to the U-shaped rail 14 in the bridge region 11' and extends between the oppositely disposed edges 13' of the bulges 13 and sealingly covers the bulges 13 in the regions 11'. Threaded securing studs 18 which extend vertically and downwardly are arranged on the bridging plates 15 and on the cover in the region adjacent the bulges 13. The threaded securing studs 18 pass through corresponding bores of a filter cloth 17 and of a perforate sheet 16. Securing nuts 19 secure the filter cloth 17 and the perforate sheet 16 to the bridging plates 15 and to the cover 12.

As seen in FIGS. 4 to 6 a separate filter cloth 17 and perforate plate 16 are provided for each bulge 13. It would however also be possible, in analogy to the preceding embodiment, to use a single filter cloth 17 and a single perforate sheet 16 which extend over both bulges 13 and the region which lies therebetween.

As seen in FIGS. 4 to 6 the perforated region of the perforate sheet 16 projects inwardly somewhat relative to the marginal region 16', which is not however essential. On the contrary the perforate part of the perforate sheet 16 can also be located in the same plane as the edge 16'.

The use and manner of operation of the embodiment of FIGS. 4 to 6 takes place in analogy with the initially described embodiment.

I claim:

1. A sterilising container comprising a container part which is open at the top and a cover which has no openings and which is sealingly mounted on the container via a ring seal, the cover having a peripheral downwardly extending edge and at least one bulge which extends up to the edge and which forms a free flow passage from the atmosphere up to a filter or valve arrangement provided at the inner side of the cover and arranged between the internal chamber and the flow channel, characterised in that the ring seal (11) is arranged at the inner side of the cover (12) in the corner between the cover surface and the edge (20), bridges the bulge (13) and is spaced therefrom; and in that the filter and valve arrangement extends in a surface region which is bounded by the seal part (11') which bridges the bulge (13) and by the edges (13') of the bulge (13) which extend within the ring seal (11), whereby the part of the surface region which is not taken up by the filter or valve arrangement is covered in gas-tight manner.

2. A sterilising container in accordance with claim 1, characterised in that the ring seal (11) includes a U-shaped rail (14) which is directly secured to the inner side of the cover (12), other than in the region of the bulge (13), and in that a sealing rope (21) is inserted into the rail (14) and preferably secured there.

3. A sterilising container in accordance with claim 2, characterised in that a respective sheet metal bridging plate (15) is secured to each of the part of the U-shaped rail (14) which bridge the bulge (13), with each bridging plate (15) extending over the associated bulge (13) and being sealingly connected with the edges (13') thereof; and in that the filter or valve arrangement is sealingly secured to these bridging plates (15) and to the regions of the cover adjacent the bulge (13).

4. A sterilising container in accordance with claim 1, characterised in that the filter or valve arrangement is formed by a perforated metal sheet (16) and by a filter cloth (17) which at least bridges the bulge (13) within the ring seal (11).

5. A sterilising container in accordance with claim 4, characterised in that the perforated sheet (16) has an edge (16') free of perforations which lies on the inner side of the cover (12) outside of the bulge (13) and/or on the bridging plate (15) which bridges the bulge (13) and is secured thereto while trapping the filter cloth (17).

6. A sterilising container in accordance with claim 5, characterised in that threaded securing studs (18) onto which nuts (19) are screwed extend inwardly at right angles to the surface of the cover from the cover (12) or from the cover plate (15) through corresponding bores of the filter cloth (17) or of the edge (16') of the perforated sheet (16).

7. A sterilising container in accordance with claim 1, in which the ring seal comprises a sealing rope inserted directly into the corner between the surface of the cover and the edge of the cover and an inner sheet metal ring support which is secured to the cover and projects at right angles to the cover surface, characterised in that the sheet metal ring support (22) is constructed in the region of the bulge (13) as the one side wall of a U-shaped rail (14'), which is secured to the cover (12) and which bridges the bulge (13), and the other side wall (22') of which extends inside the bulge (13) parallel to the edge (20) and there supports the sealing rope (21) laterally from the outside.

8. A sterilising container in accordance with claim 7, characterised in that a frame (23) which carries the filter or valve arrangement is sealingly secured to the U-shaped rail (14') and to the regions of the cover (12) which surround the bulge or bulges (13).

9. A sterilising container in accordance with claim 8, characterised in that the frame (23) carries inwardly projecting threaded securing studs (18) on which a filter cloth (17) provided with corresponding bores and a perforated sheet of metal (16), which covers the filter cloth and is likewise provided with appropriate bores, are mounted and secured there to the frame (23) by nuts (19).

10. A sterilising container in accordance with claim 1, characterised in that the or each bulge (13) extends up to the lower lip of the edge (20).

11. A sterilising container in accordance with claim 1, characterised in that the or each bulge (13) extends parallel to the side of the cover (12) which carries the cover securing members (24).

12. A sterilising container in accordance with claim 1, characterised in that the or each bulge (13) is formed by material which is displaced outwardly parallel to itself from the plane of the cover (12) and. from the plane of the edge (20), with this material merging into the material lying in the normal plane of the cover (12) at the edge regions (13') of the respective bulge.

13. A sterilising container in accordance with claim 1, characterised in that the edges (13') of the or each bulge (13) are parallel to one another.

14. A sterilising container in accordance with claim 1, characterised in that the edge regions (13) of the or each bulge (13) extend at right angles to the side or sides.

15. A sterilising container in accordance with claim 1, characterised in that the or each bulge (13) extends transversely over the cover (12) to opposite edges (20) thereof; and in that the cover plate (15) or the U-shaped rails (14, 14') are correspondingly provided in duplicate.

16. A sterilising container in accordance with claim 1, characterised in that, in particular for rectangular covers (12) a plurality and in particular two bulges are arranged spaced apart in the direction of the longitudinal sides of the cover, preferably parallel to the short sides thereof.

17. A sterilising container in accordance with claim 7, characterised in that a plurality of bulges is provided; in that the frame (23) and the U-shaped rails (14') extend over all bulges (13) and the cover regions that lie therebetween; and in that the frame (23) is inwardly joggled in such a way that the filter cloth (17) and the perforated sheet (16) are also spaced from the inner surface of the cover in the region between the bulges (13).

18. A sterilising container in accordance with claim 8, characterised in that the cover plate (15), the U-shaped rails (14, 14'), the sheet metal support ring (22) and/or the frame (23) are welded to the part to which they are to be secured.

* * * * *

UNITED STATES PATENT AND TRADEMARK OFFICE
CERTIFICATE OF CORRECTION

PATENT NO. : 4,512,498

DATED : April 23, 1985

INVENTOR(S) : Karl Leibinger

It is certified that error appears in the above-identified patent and that said Letters Patent is hereby corrected as shown below:

On the front page of the printed patent, the Assignee's name is spelled incorrectly. Please delete "Karl Liebinger Medizintechnik GmbH & Co." and insert therefor --Karl Leibinger Medizintechnik GmbH & Co.--.

Signed and Sealed this

Twenty-eighth Day of January 1986

[SEAL]

Attest:

DONALD J. QUIGG

Attesting Officer

Commissioner of Patents and Trademarks